United States Patent [19]

Roberts et al.

[11] Patent Number: 4,640,614
[45] Date of Patent: Feb. 3, 1987

[54] TESTING SAMPLES

[75] Inventors: David Roberts, Maple Durham, Near Reading; Michael R. Williams, Stokenchurch, both of United Kingdom

[73] Assignee: Ranks Hovis McDougall plc, United Kingdom

[21] Appl. No.: 679,570

[22] Filed: Dec. 7, 1984

[30] Foreign Application Priority Data

Dec. 7, 1983 [GB] United Kingdom ............... 8332675

[51] Int. Cl.$^4$ ............................................. G01N 21/01
[52] U.S. Cl. .................................... 356/36; 73/863.57; 250/341; 250/343; 250/358.1
[58] Field of Search ............... 356/36, 38; 73/169, 73/863.51, 863.57, 863.71, 863.52; 250/341, 359.1, 343, 338 R, 576, 358.1, 339

[56] References Cited

U.S. PATENT DOCUMENTS

| 3,241,371 | 3/1966 | Horeth | 73/863.57 |
| 3,250,128 | 5/1966 | Cassel | 73/863.51 |
| 3,328,587 | 6/1967 | Brown et al. | 250/358.1 |
| 3,575,055 | 4/1971 | Thornton, Jr. | 73/863.57 |
| 4,180,331 | 12/1979 | Lundstrom | 356/445 |
| 4,400,086 | 8/1983 | Webster | 356/36 |
| 4,479,055 | 10/1984 | Perten | 250/343 |

Primary Examiner—Carolyn E. Fields
Attorney, Agent, or Firm—McCormick, Paulding & Huber

[57] ABSTRACT

A method of and apparatus for testing a sample of particulate material, for example, flour by the use of a Near Infra-Red Reflectance Spectrometer, which includes permitting the material to fall freely into a trap having an openable and closable top and bottom whereby sample material caught in the trap may be tested, means being provided for purging the trap between samples.

2 Claims, 5 Drawing Figures

4,640,614

TESTING SAMPLES

INTRODUCTION

This invention relates to a method of and apparatus for testing samples of particulate material.

BACKGROUND

In the control and monitoring of a modern food factory, there is a need for the rapid analysis of several parameters of the raw materials and the final product such as protein and fat content, moisture and colour. Historically, such measurements have been carried out batchwise in a laboratory using conventional physical and chemical techniques and these take many hours or even days to complete. The raw materials and food products analysed can include milk powders, egg products, wheat, flour, cake mixes, starches and other farinaceous products.

Over the past few years, modern technology has provided instruments that have gone some way to providing the rapid analysis required. Examples of such instruments are various forms of spectrometer, for example, a reflectance spectrometer. These instruments are non-destructive on the sample and depend on irradiating the sample with waves of a particular frequency and measuring the reflected radiation which may be attenuated according to the characteristics of the sample under test. An example of such an instrument is a Near Infra-Red Reflectance Spectrometer (hereinafter called "N.I.R.").

When such instruments are used in the laboratory to test samples of particulate food materials, careful packing and cleaning of the sample cell is of paramount importance as surface imperfections and carry-over of one sample to another lead to unreliable results. In addition to sample preparation, there is still the onerous task of sampling reliably both raw material and product at regular intervals to obtain a representative picture of their composition.

OBJECT OF THE INVENTION

It is the main object of this invention to provide a method and apparatus for the testing of a sample of particulate material in which there is automatic collection and presentation and disposal of the sample to a remote instrumental measuring head.

STATEMENTS OF INVENTION

According to the present invention there is provided a method of testing a sample of particulate material which includes permitting a continuous stream of the material to fall freely, closing the top of a sample trap positioned in the stream, said trap having a closable top and bottom, purging the interior of the trap so that remnant material falls through the open bottom, closing the bottom of the trap and opening the top of the trap, permitting a sample mass of material to accumulate in the trap and testing the sample mass by instrumental means.

Conveniently, the testing is carried out with N.I.R.

The invention also includes the method as above in which after a sample mass of material has accumulated in the trap at least a portion thereof is compacted and the testing carried out on the compacted material.

The invention also includes apparatus for testing a sample of particulate material permitted to fall freely in a constant stream, including a sample trap adapted to be located in the stream of material, the trap having an open top and an open bottom with movable closures for selectively opening and closing the top and bottom, means for purging the interior of the trap so that remnant material falls through the open bottom of the trap and instrumental means for testing sample material in the trap.

Conveniently, the testing means uses N.I.R.

Conveniently, the apparatus as described is also provided with compaction means so that at least a portion of a sample mass of material accumulated in the trap may be compacted for testing. The compaction means may be in the form of (but not limited to) a ram, Archimedean screw or a spring device.

DRAWINGS

SPECIFIC DESCRIPTION

Figure 1:
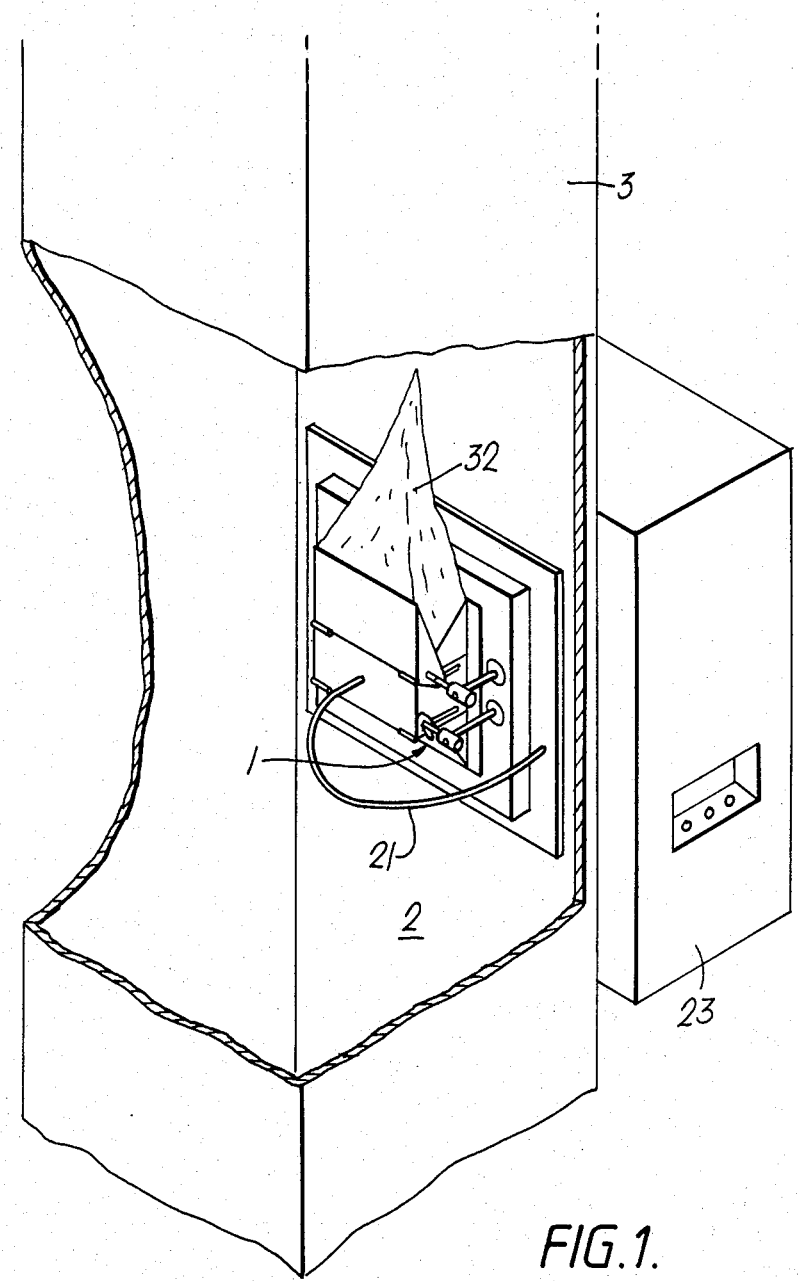
FIG. 1 is a part sectioned perspective view of apparatus constructed in accordance with the invention.
Figure 2:
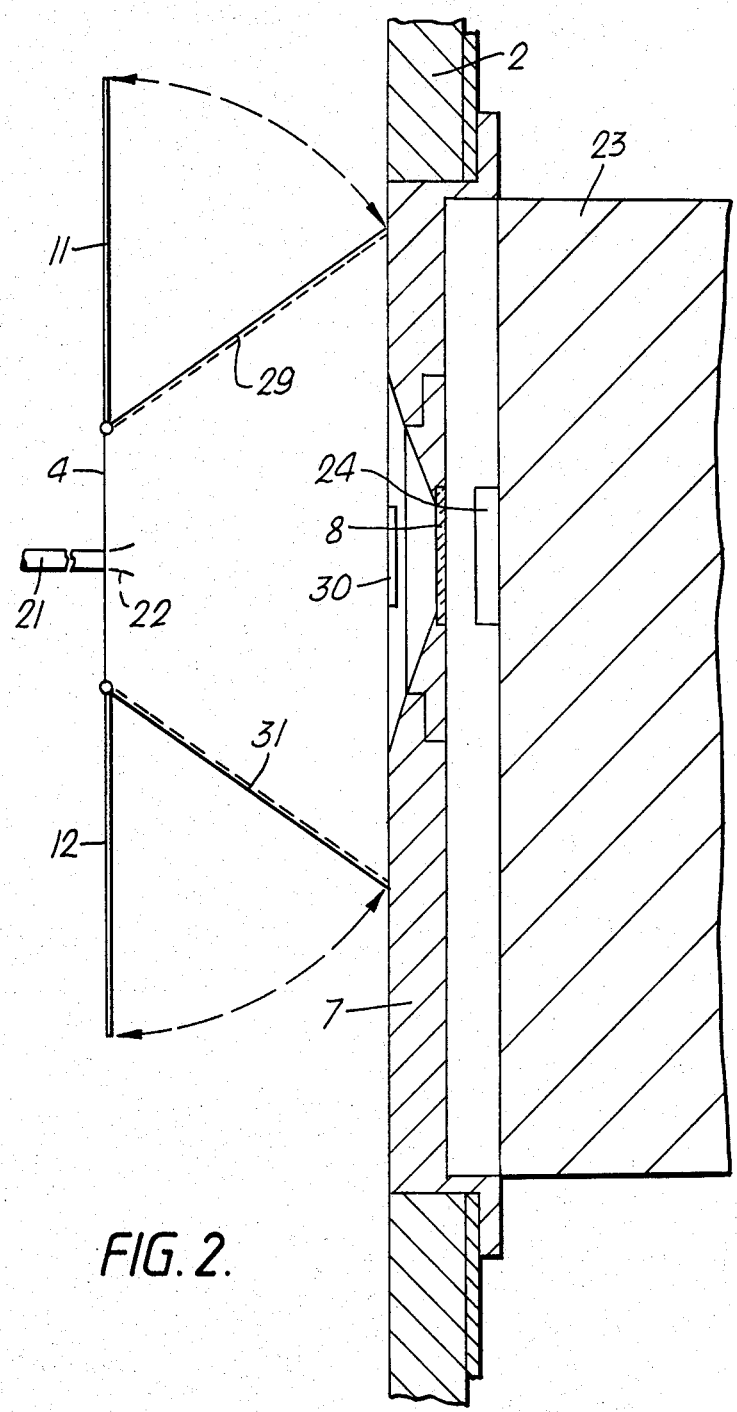
FIG. 2 is a diagrammatic side elevation of the apparatus shown in FIG. 1.
Figure 3:
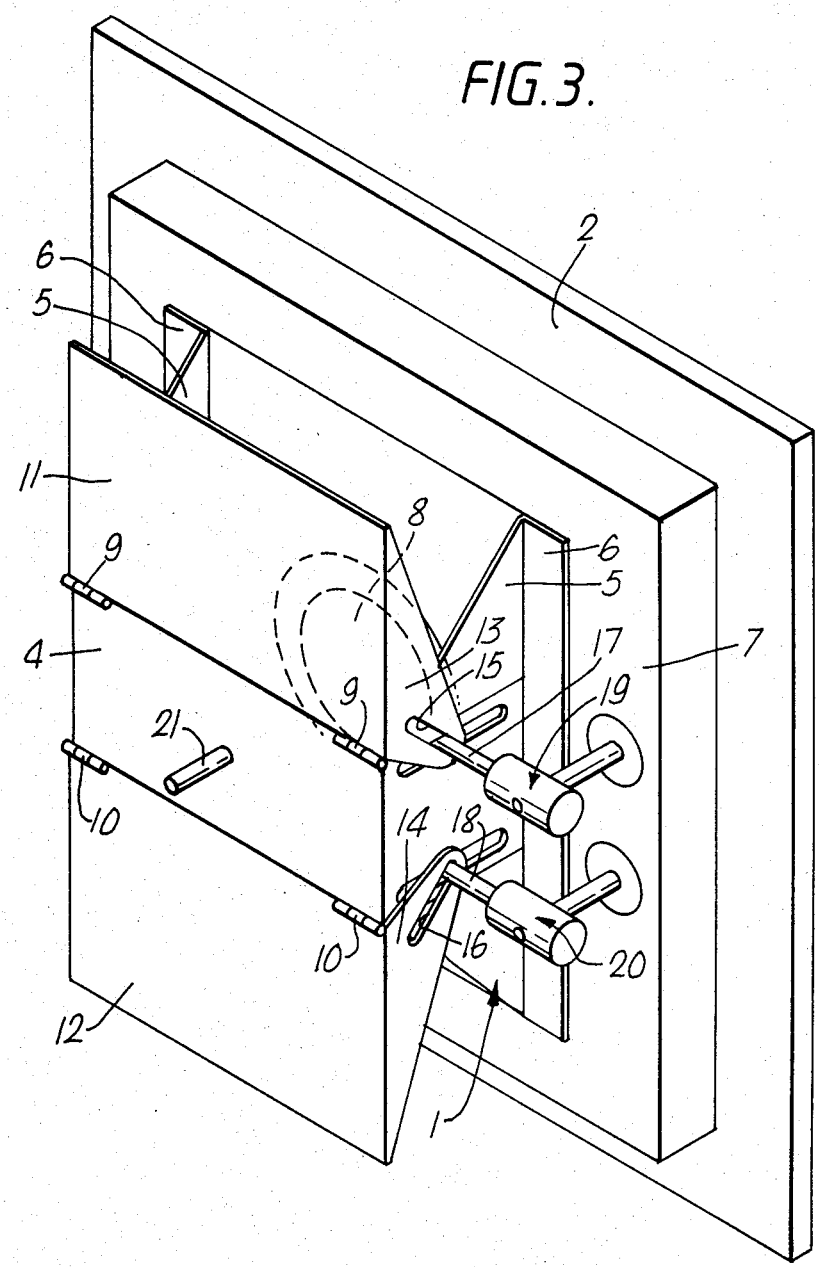
FIG. 3 is an enlarged perspective view of part of the apparatus shown in FIG. 1.

Referring first to FIGS. 1 to 3, a sample trap 1 is located on one wall 2 of a chute 3 down which particulate material is permitted to fall freely. The sample trap 1 has a horizontal cross sectional area much smaller than the horizontal cross-sectional area of the chute comprises a front wall 4 and side walls 5 having flanges 6 for connecting the sample trap to a mounting panel 7 having an aperture filled with a glass panel 8.

Hingedly mounted on front panel 4 by hinges 9 and 10 are top closure 11 and bottom closure 12 having arms 13 and 14 respectively with slots 15 and 16 into which project flanges 17 and 18, respectively, of operating devices 19 and 20.

A pneumatic pipeline 21 passes through front panel 4 and connects to a "fishtail" air distributor 22 within the sample trap.

Positioned remote from the sample trap 1 i.e., on the other side of panel 2 is a measuring device 23, for example, a device using N.I.R., having a reading head 24.

Figure 5:
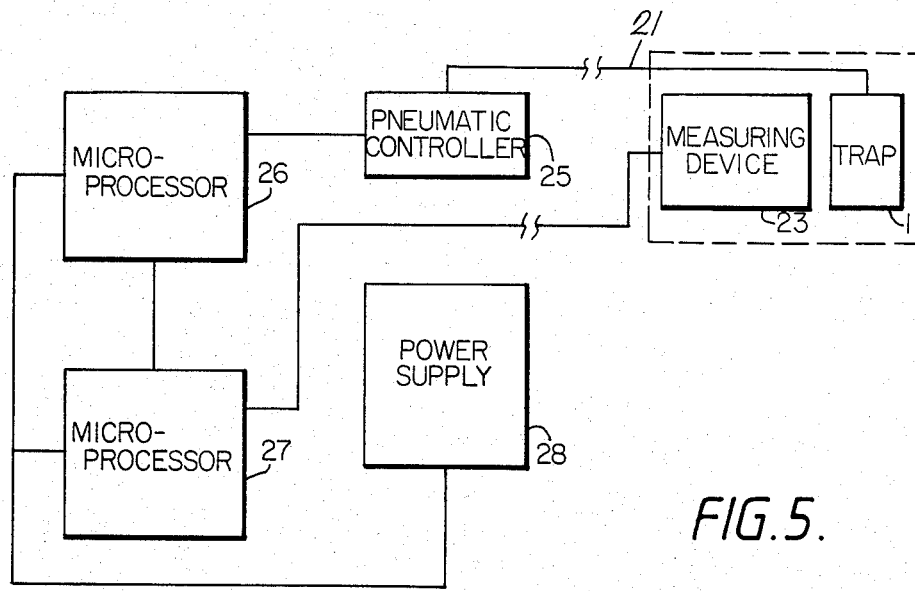
FIG. 5 is a block diagram depicting the connection of various parts of the apparatus.

The apparatus is connected as illustrated in FIG. 5 in which the sample trap and measuring device are indicated. Connected to the sample trap by pipe 21 is a pneumatic controller 25 which is controlled by a microprocessor 26. The measuring device 23 is also controlled by a microprocessor 27, the two microprocessors 26 and 27 being powered from a power supply 28.

The whole apparatus is housed in an enclosure under positive pressure and is constructed to afford protection against possible dust explosions.

All mechanical parts external to the main enclosure are pneumatically operated from within the enclosure through appropriate dust seals and are all electrically earthed to prevent the build-up of static charge on the apparatus, again to provide protection against possible dust explosions.

In operation and on command from the microprocessor 26, closure 11 briefly closes and reopens to remove any build-up of flour from its surface. Closure 11 is then closed to the position illustrated at 29 in FIG. 2 and an air purge from vent 22 creates a cone of air across the whole sample trap. Additional purge vents 30 may be provided to create a fishtail of air across the glass window 8. The combination of these flow patterns creates considerable turbulence in the partially closed sample trap and air scrubs the surface clean thus effectively purging the interior of the trap so that remnant material falls through the open bottom of the trap.

The closure 12 is now closed to the position indicated at 31 in FIG. 2 and the air purge ceases. The top closure 11 is now opened and the sample trap is allowed to fill with particulate material falling freely down chute 3 under gravity. A smooth evenly packed sample builds up within the sample trap as indicated at 32 in FIG. 1. After an appropriate interval of time, the measuring sequence is initiated by microprocessor 27 and the measurements processed.

The bottom closure 12 is now opened and the air purge again started, this effectively fluidising the contents of the sample trap which fall away through the bottom of the trap to rejoin the bulk of the material.

The process is then repeated according to the program set in the micrprocessors and typical sample interval time may range from one minute to several hours.

The whole sampling sequence may be overridden manually to enable maintenance to be carried out without interruption of the particulate material stream.

Detectors may be placed on all moving parts to ensure that in the event of any failure there is total shutdown of the system to prevent the possibility of dust explosions.

Attention must be paid to the intrinsic requirements of the measuring process in terms of sample window material, distance of the measuring head from the sample window and automatic self-calibration checking. The sample window 8 may be of optical glass which may or may not be made electrically conductive by the vacuum deposition of oxides of tin.

Provision may be made for the insertion of a thin ceramic white tile to enable self checking to be carried out. This may again be microprocessor controlled and may be programmed to operate when required.

Figure 4:
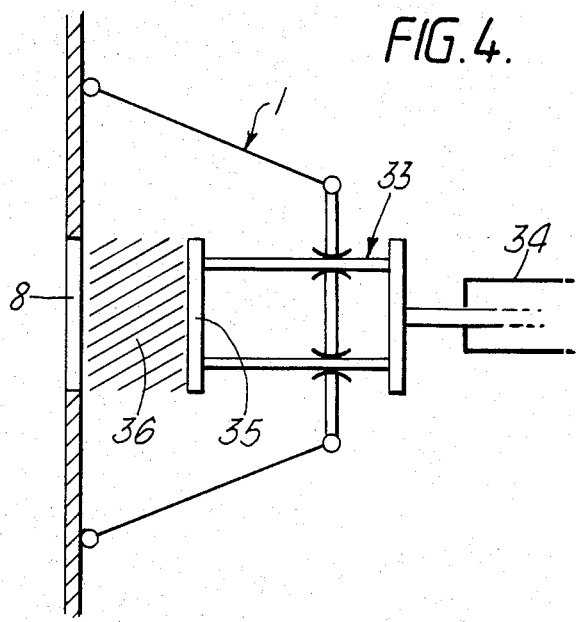
FIG. 4 is a diagrammatic side elevation of a modified form of apparatus constructed in accordance with the invention.

A modification of the sample trap is illustrated in FIG. 4 in which a compaction device 33 is provided. This comprises a ram 34 with a compaction head 35 so positioned that when the ram is operated a portion 36 of the particulate material which has accumulated within the trap 1 is compressed to a predetermined degree. This device overcomes any errors due to particle size in that it packs down the relevant portion of material immediately in the vicinity of the window 8. The ram 34 may be operated pneumatically or this device may be replaced by a similar compaction means, for example, an Archimedean screw or spring device.

The apparatus may be modified from those described above, for example, in less hazardous conditions the pneumatic control may be replaced by electrical or electromechanical control and the head and sampling device may be entirely remote from the rest of the control electronics.

The invention may be used on line on any powdered product that is suitable for analysis by instrumental methods using radiation, for example, animal feedstuffs, flour, milk powders, egg products, soya products, cement or lime.

We claim:

1. A method of testing a sample of particulate material which includes permitting a continuous stream of the material to fall freely through a vertical chute having at least one sidewall and a given horizontal cross-sectional area, positioning in said vertical chute a trap having vertical wall members defining a trap chamber having a horizontal cross-sectional area much smaller than the horizontal cross-sectional area of said chute, said trap chamber having a top and a bottom which allow a portion of said stream of particulate material to fall through said trap chamber when both said top and bottom are open, one of said vertical wall members of said trap being a portion of said one side wall of said chute and having a window made of transparent material, said trap including a top closure member movable relative to said vertical wall members between an open position at which the top of said chamber is open to receive material from said stream and a closed position at which the top of said chamber is closed to prevent the entry of material from said stream, and said trap also including a bottom closure member movable relative to said vertical wall members between an open position at which the bottom of said chamber is open to permit material to fall from said chamber into said stream and a closed position at which the bottom of said chamber is closed to prevent material from falling from said chamber, moving said top closure member to its closed position and said bottom closure member to its open position, then purging said trap chamber by flowing air into said trap chamber to loosen remnant material and permit it to fall through the now open bottom of said trap chamber, then terminating said flow of air and thereafter moving said bottom closure member to its closed position and said top closure member to its open position and permitting a sample mass of material to accumulate in said trap chamber, and then testing said sample mass through said window by instrumental means located outside of said chute.

2. Apparatus for testing a sample of particulate material permitted to fall freely in a constant stream through a vertical chute having at least one sidewall and a given horizontal cross-sectional area, said apparatus comprising: a sample trap located in the stream of material, said trap having vertical wall members defining a trap chamber having a horizontal cross-sectional area much smaller than the horizontal cross-sectional area of said chute, said trap chamber having a top and a bottom which allow a portion of said stream of particulate material to fall through said trap chamber when both said top and bottom are open, one of said vertical wall members of said trap being a portion of said one side wall of said chute and having a window made of transparent material, said trap including a top closure member movable relative to said vertical wall members between an open position at which the top of said chamber is open to receive material from said stream and a closed position at which the top of said chamber is closed to prevent the entry of material from said stream, and said trap also including a bottom closure member movable relative to said vertical wall members between an open position at which the bottom of said chamber is open to permit material to fall from said chamber into said stream and a closed position at which the bottom of said chamber is closed to prevent material from falling from said chamber, means for moving said top and bottom closure members between a first condition in which said top member is in its closed position and said bottom member is in its open position and a second condition in which said bottom member is in its closed position and said top member is in its open condition to permit a sample mass of material to accumulate in said trap chamber, means for flowing air into said trap chamber while said top and bottom closure members are in said first condition so as to loosen remnant material and permit it to fall through the open bottom of said chamber, and instrumental means located outside of said chute for testing through said window sample material accumulated in said trap chamber.

* * * * *